(12) United States Patent
Kim et al.

(10) Patent No.: US 8,541,212 B2
(45) Date of Patent: Sep. 24, 2013

(54) GENETIC MODIFICATION FOR PRODUCTION OF 3-HYDROXYPROPIONIC ACID

(75) Inventors: Jae Young Kim, Suwon-si (KR); Jae Chan Park, Yongin-si (KR); Sung Min Park, Yongin-si (KR); Hyun Min Koo, Seoul (KR); Byung Jo Yu, Hwaseong-si (KR); Hwa Young Cho, Hwaseong-si (KR); Young kyoung Park, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days.

(21) Appl. No.: 13/368,953

(22) Filed: Feb. 8, 2012

(65) Prior Publication Data

US 2012/0329110 A1 Dec. 27, 2012

(30) Foreign Application Priority Data

Jun. 27, 2011 (KR) ........................ 10-2011-0062312

(51) Int. Cl.
*C12P 7/62* (2006.01)

(52) U.S. Cl.
USPC ........................................ 435/135; 435/252.3

(58) Field of Classification Search
USPC ................................................ 435/135, 252.3
See application file for complete search history.

(56) References Cited

FOREIGN PATENT DOCUMENTS

| KR | 20090127516 A | 12/2009 |
|---|---|---|
| WO | WO 2008/091627 A2 | 7/2008 |
| WO | WO 2009/089457 A1 | 7/2009 |
| WO | WO 2010/011874 A2 | 1/2010 |

*Primary Examiner* — Maryam Monshipouri
(74) *Attorney, Agent, or Firm* — Leydig, Voit & Mayer, Ltd

(57) ABSTRACT

A method of increasing 3-HP production efficiency by inhibiting expression of a lactate dehydrogenase, a phosphotransacetylase, and an alcohol dehydrogenase in production of 3-HP using a malonic semialdehyde reduction pathway to prevent metabolite leak and increase a malonyl-CoA pool is disclosed.

19 Claims, 5 Drawing Sheets

SEQUENCE LISTING

```
<160> NUMBER OF SEQ ID NOS: 2

<210> SEQ ID NO 1
<211> LENGTH: 34
<212> TYPE: DNA
<213> ORGANISM: Escherichia coli

<400> SEQUENCE: 1
aattccatgg gacgaattgg cataccaaga gaac                              34

<210> SEQ ID NO 2
<211> LENGTH: 34
<212> TYPE: DNA
<213> ORGANISM: Escherichia coli

<400> SEQUENCE: 2
aattggattc ttacagagct ttcaggattg catc                              34
```

GENETIC MODIFICATION FOR PRODUCTION OF 3-HYDROXYPROPIONIC ACID

CROSS-REFERENCE TO RELATED APPLICATION

This application claims priority to Korean Patent Application No. 10-2011-0062312, filed on Jun. 27, 2011, and all the benefits accruing therefrom under 35 U.S.C. §119, the content of which in its entirety is herein incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 588 Byte ASCII (Text) file named "709220SequenceListing.TXT," created on Feb. 8, 2012.

BACKGROUND

Recently, production of bio-based fuels has become imperative due to the rapid increase in the prices of petroleum and serious environmental pollution. Biodiesel, one of the bio-based fuels, is produced by transesterification of a triglyceride from vegetable oils or animal fats.

Mass production of biodiesel has resulted in large-scale production of glycerol as a by-product with about 7.7 billion pounds of glycerol produced per 1 billion gallons of biodiesel. The production of glycerol has increased very rapidly and is estimated at about 3.2 billion pounds per year in the United States and 8 billion pounds per year worldwide. As a consequence, the price of glycerol has decreased almost ten-fold over the past 2 years. The market price of crude glycerol was 5 to 15 cents/lb in 2004, but is now reportedly less than 2.5 cents/lb. In comparison, the price of glucose is currently about 5 cents/lb and is increasing gradually. Should the current trend continue, the continuous decrease in the price of glycerol might be considered inevitable.

A microorganism may use glycerol as a carbon source and generate various fermentation products using the glycerol. 3-Hydroxypropionic acid ("3-HP"; $C_3H_6O_3$—MW 90.08) is a compound applicable to various chemical processes, which may be produced from a renewable resource such as glycerol. 3-HP may be produced by both chemical synthetic methods and biological methods.

The chemical methods to produce 3-HP may include (1) a method of producing 3-HP by using palladium as a catalyst from 1,3-propanediol as a starting material, (2) a method of producing 3-HP in presence of palladium and platinum as catalysts from 3-hydroxypropionaldehyde, and (3) a method of producing 3-HP (e.g., with a selectivity of 91% and a yield of 34%) by reaction of an acrylic acid as a starting material with an ion exchange resin (Amberlyst™ 15) as a solid acid catalyst at 100° C. for 40 hours in a high-pressure reaction vessel.

However, most of these chemicals are toxic and carcinogenic. In addition, the chemicals consume a large quantity of energy under high temperature and pressure and exhaust a large quantity of pollutants.

Biological 3-HP production can be performed by a photoheterotrophic microorganism, such as *Chloroflexus aurantiacus*. This microorganism is grown autotrophically or photoheterotrophically to produce 3-HP as an intermediate. Other known microorganisms producing 3-HP from glycerol include *Desulfovibrio carbinolicus*, *D. fructosovorans*, *Lactobacillus reuteri*, *Pelobacter venetianus*, *Ilyobacter polytropus*, etc.

However, because of a complicated metabolic pathway, it is difficult to effectively control a process and a decrease in production yield and producibility is expected.

Therefore, there is a desire to produce 3-HP by alternative means.

SUMMARY OF THE INVENTION

An effective biosynthetic pathway wherein various gene manipulations are effected to improve production yield and producibility of 3-HP is provided.

According to one aspect, increasing 3-HP production efficiency is achieved by inhibiting expression of a lactate dehydrogenase, a phosphotransacetylase and an alcohol dehydrogenase in the production of 3-HP using a malonic semialdehyde reduction pathway to prevent metabolite leak and increase a malonyl-CoA pool.

As a recombinant microorganism for producing 3-HP using the malonic semialdehyde reduction pathway, a recombinant microorganism for producing 3-HP subjected to gene manipulation to prevent leak of an intermediate metabolite is provided.

For example, a recombinant microorganism for producing 3-HP in which a gene encoding at least one selected from the group consisting of the lactate dehydrogenase, the phosphotransacetylase and the alcohol dehydrogenase is deleted or knocked out is provided.

According to another aspect, an improved method of producing 3-HP using the recombinant microorganism may be provided.

In an example, as a recombinant microorganism for producing 3-HP including a pyruvate→acetyl-CoA→malonyl-CoA→malonic semialdehyde pathway, that is, a pathway in which metabolites are sequentially produced in a sequence of pyruvate, acetyl-CoA, malonyl-CoA and malonic semialdehyde, a recombinant microorganism for producing 3-HP in which a gene encoding at least one selected from the group consisting of the lactate dehydrogenase, the phosphotransacetylase and the alcohol dehydrogenase is deleted or knocked out is provided.

Here, the gene coding for the lactate dehydrogenase may be ldhA or a homolog or variant thereof, and the gene coding for the phosphotransacetylase may be pta or a homolog or variant thereof. In addition, one specific example of the alcohol dehydrogenase may be ethanol dehydrogenase, and a gene coding for the ethanol dehydrogenase may be adhE or a homolog or variant thereof.

In another example, the recombinant microorganism includes those in which the genes encoding the lactate dehydrogenase, the phosphotransacetylase, and the alcohol dehydrogenase are all deleted or knocked out. That is, in an exemplary embodiment, a recombinant microorganism in which one or at least two of the ldhA, pta and adhE genes are deleted or knocked out is used.

The recombinant microorganism reduces or inhibits conversion of pyruvate into lactate, conversion of acetyl-CoA into acetate via acetyl phosphate ("acetyl P"), or conversion of acetyl-CoA into ethanol due to inhibition of the activities of the enzymes.

The microorganism may be a microorganism included in the genera of *Escherichia*, *Saccharomyces* and *Kluyveromyces*, and in an exemplary embodiment, *E. coli* is used.

In addition, the recombinant microorganism according to an exemplary embodiment produces 3-HP using the malonic semialdehyde reduction pathway including a pyruvate→acetyl-CoA→malonyl-CoA→malonic semialdehyde pathway, and thus includes a gene encoding for an enzyme reducing malonyl-CoA into malonic semialdehyde and a gene encoding for an enzyme reducing malonic semialdehyde into 3-HP.

Here, the gene encoding for an enzyme reducing malonyl-CoA into malonic semialdehyde is a gene encoding for a malonyl-CoA reductase ("mcr"), and the gene encoding for an enzyme reducing malonic semialdehyde into 3-HP may be a gene encoding for a malonate semialdehyde reductase ("msr").

In addition, to solve redox imbalance, the recombinant microorganism may further include genes encoding for an NADPH ("nicotinamide adenine dinucleotide-phosphate") regeneration enzyme.

The gene encoding for the NADPH regeneration enzyme may be a gene encoding for a transhydrogenase or a gene encoding for a glyceraldehyde-3-phosphate dehydrogenase.

For example, the gene encoding for the transhydrogenase may be pntAB ("pyridine nucleotide transhydrogenase") or udhA (soluble pyridine nucleotide transhydrogenase), and the gene encoding for the glyceraldehyde-3-phosphate dehydrogenase may be gapN (non-phosphorylating glyceraldehyde-3-phosphate dehydrogenase).

Further, in another aspect, a method of producing 3-HP is provided, which uses a microorganism process performing a metabolic pathway including: converting pyruvate into acetyl-CoA; converting acetyl-CoA into malonyl-CoA; converting malonyl-CoA into malonic semialdehyde; and converting malonic semialdehyde into 3-HP, wherein, during the conversion of pyruvate into acetyl-CoA, an activity of at least one enzyme selected from the group consisting of the lactate dehydrogenase, the phosphotransacetylase and the alcohol dehydrogenase is inhibited.

As described above, the inhibition of the enzyme activity may be performed by deletion or knockout of at least one gene of adhE, pta and adhE, and particularly, this method may prevent leak of an intermediate metabolite of the metabolic pathway and thus increase malonyl-CoA pools in a microbial cell.

The method may be performed by incubating the recombinant microorganism above in a medium containing a carbon substrate.

The carbon substrate includes at least one selected from the group consisting of glucose, sucrose, cellulose and glycerol, and in an exemplary embodiment, glucose is used.

Descriptions of other factors in the method are described above.

In the production of 3-HP using the malonic semialdehyde reduction pathway, expression of the lactate dehydrogenase, expression of the phosphotransacetylase and/or the alcohol dehydrogenase is inhibited, thereby preventing metabolite leak of an intermediate metabolite to increase malonyl-CoA pools and noticeably increasing 3-HP production efficiency. Thus, this method is very useful in producing a biofuel.

BRIEF DESCRIPTION OF THE DRAWINGS

The above and other aspects of this disclosure will become more readily apparent by describing in further detail non-limiting exemplary embodiments thereof with reference to the accompanying drawings, in which.

DETAILED DESCRIPTION OF THE INVENTION

Figure 1:
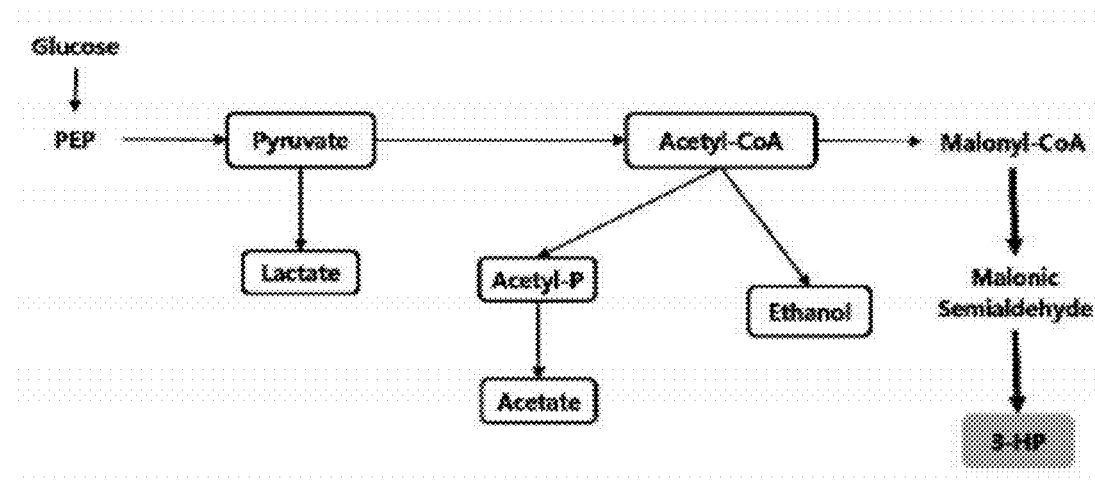
FIG. 1 is a diagram illustrating a relationship between the metabolic pathway producing 3-HP and the intermediate leak leading to the production of lactate, acetyl-P/acetate, and/or ethanol.

Definitions of terms used herein are as follows:

The term "metabolically engineered" or "metabolic engineering" involves rational pathway design and assembly of biosynthetic genes, genes associated with operons and control elements of such polynucleotides, to produce or increase production of a desired metabolite from a microorganism. "Metabolically engineered" may further include optimization of metabolic flux by regulation and optimization of transcription, translation, protein stability, and protein functionality using genetic engineering and suitable culture condition including reduction, disruption, or knocking out of a competing metabolic pathway that competes for an intermediate leading to the desired pathway. A biosynthetic gene can be heterologous to the host microorganism, either by virtue of being foreign to the host, or by being modified by mutagenesis, recombination, and/or association with a heterologous expression control sequence in an endogeneous host cell. In one aspect, when a gene is xenogenetic to the host organism, the polynucleotide for the gene can be codon-optimized for the host cell.

The term "conditions for an enzyme reaction" refers to arbitrary conditions (for example, temperature, pH, a non-inhibitory material, etc.) usable in an environment that allow an enzyme to function catalytically. The conditions for the enzyme reaction may be in vitro or in vivo conditions, such as conditions in a test tube or in a cell.

The term "substrate" refers to any substance or compound that is converted or meant to be converted into another compound by action of an enzyme. The term includes not only a single compound, but also combinations of compounds, such as solutions, mixtures, and other materials which contain at least one substrate or derivative thereof. Further, the term "substrate" encompasses not only compounds that provide a carbon source suitable for use as a starting material, such as any biomass-derived sugar, but also intermediate and end product metabolites used in a pathway of a metabolically engineered microorganism as described herein. A substrate encompasses suitable carbon substrates ordinarily used by microorganisms.

The term "protein" includes a fragment, analog, and derivative of a protein having essentially the same biological activity or function as a reference protein.

The expression "encoded by" or "coding for" is used to explain that a sequence of a nucleic acid codes for a polypeptide sequence. Here, the polypeptide sequence includes an amino acid sequence composed of at least 3 to 5 amino acids or more, at least 8 to 10 amino acids or more, or 15 to 20 amino acids or more, which are polypeptides encoded by the nucleic acid sequence. The polypeptide sequence also includes a polypeptide sequence immunologically identified using a polypeptide encoded by the sequence. Therefore, an antigen "polypeptide, protein, or amino acid" sequence may have a similarity of approximately 70% or more, 80% or more, or 90 or 95% or more, or 99% or more with respect to a polypeptide or amino acid sequence of the antigen.

The term "gene" refers to a nucleotide sequence of a nucleic acid molecule (chromosome, plasmid, etc.) related to a genetic function. The gene is a genetic unit of an organism including, for example, a polynucleotide sequence taking a specific physical location ("genetic locus") in a genome of the organism (for example, a DNA sequence of a mammal). The gene may code for an expression product such as a polypeptide or polynucleotide. Generally, the gene includes a coding sequence such as a polypeptide coding sequence or a non-coding sequence such as a promoter sequence, a polyadenylated sequence, or a transcription control sequence (e.g., an enhancer sequence). Genes of various eukaryotic organisms have "exons (coding sequences)" into which an "intron (non-coding sequence)" is interposed.

The term "gene targeting" refers to a genetic technique of disrupting or inserting a specific gene in an organism by homologous recombination, and may cause targeted knockout of a gene encoding an enzyme. The "knockout" of a gene refers to partial, substantial, or complete deletion, disruption, silencing, inactivation, or down-regulation of the gene. Herein terms such as targeting, deletion, and disruption are used interchangeably.

The term "transformation or transfection" refers to the process by which a exogenous DNA is introduced into a host cell. The term "transfected cell" refers to a cell having a exogenous DNA by introducing the DNA into the cell. When DNA is introduced into the cell, a nucleic acid may be inserted into a chromosome or replicated into an extrachromosomal material.

The terms "transformation" and "transfection" refer to the process by which a heterologous DNA is introduced into a host cell. The term "transfected cell" refers to a cell having heterologous DNA introduced into the cell. When DNA is introduced into a cell, the nucleic acid may be inserted into the chromosome or replicated as extrachromosomal material.

The term "host cell" includes an individual cell or a cell culture, which serves to receive and harbor an arbitrary recombinant vector(s) or isolated polynucleotide. The host cell may be a descendant of a single host cell, and the descendant may not be completely the same as a parent cell due to natural, accidental, or artificial mutagenesis and/or variation (in an aspect of its phenotype or total DNA complement). A host cell may be transfected, transformed, or infected by a recombinant vector or polynucleotide in vivo or in vitro. A host cell including a recombinant vector is a recombinant host cell, a recombinant cell, or a recombinant microorganism.

The terms "recombinant microorganism" and "recombinant host cell" are used interchangeably herein, and refer to microorganisms that have been genetically modified, for instance, to express, underexpress (reduce expression), or overexpress (increase expression) of endogenous polynucleotides, or to express non-endogenous sequences, such as those included in a vector, or which have a reduction in expression of an endogenous gene. A polynucleotide generally encodes an enzyme involved in a metabolic pathway for producing a desired metabolite as described above. Therefore, recombinant microorganisms described herein have been genetically engineered to express, underexpress, or overexpress target enzymes, e.g., those not previously expressed, or underexpressed or overexpressed, by a parent microorganism. It is understood that the terms "recombinant microorganism" and "recombinant host cell" refer to not only the specific recombinant microorganism but to the progeny or potential progeny of such a microorganism.

The term "obtained from" or "derived from" when used in reference to a sample or a polynucleotide or polypeptide sequence means that the sample, such as a nucleotide extract or polypeptide extract, or the polynucleotide or polypeptide sequence is isolated or induced from a specific source such as a predetermined organism, typically a microorganism.

The term "heterologous" refers to a polynucleotide sequence or a polypeptide, which is introduced into a cell by a molecular biological technique, that is, a genetic engineering treatment for producing a recombinant microorganism, and not by being naturally generated from a wild-type cell or organism. A polynucleotide sequence or a polypeptide can be heterologous to a host microorganism, either by virtue of being foreign to the host, or by virtue of having an endogenous gene be subjected to modification by genetic engineering, e.g., by mutagenesis, recombination, and/or association with a heterologous expression control sequence in the endogeneous host.

The terms "approximately" and "about" are interchangeably used herein and indicate an amount, level, value, number, frequency, percent, dimension, size, weight, or length changed by 30, 25, 20, 25, 10, 9, 8, 7, 6, 5, 4, 3, 2 or 1% of the reference amount, level, value, number, frequency, percent, dimension, size, weight, or length.

It will be further understood that the terms "comprises" and/or "comprising" when used in this specification, specify the presence of steps or elements, or groups thereof, but do not preclude the presence or addition of one or more other steps or elements, or groups thereof. The terms "having", "including", and "containing" are also to be construed as open-ended terms (i.e. meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

Unless otherwise defined, all terms used herein have the same meaning as commonly understood by those skilled in the art. In addition, methods or samples are described in the specification, but methods or samples similar to or the same as those described above are also included in the scope of the invention.

This disclosure relates to a method of producing 3-HP using a recombinant microorganism. The method uses a "malonic semialdehyde reduction pathway", which reduces pyruvate into 3-HP in a sequence of pyruvate→acetyl-CoA→malonyl-CoA→malonic semialdehyde→3-HP, while inhibiting an activity of at least one enzyme selected from the group consisting of a lactate dehydrogenase, a phosphotransacetylase, and an alcohol dehydrogenase. Therefore, leak of intermediate metabolites (e.g., lactate, acetyl-P/acetate, and ethanol) is prevented and malonyl-CoA pools are increased, thereby increasing the efficiency of producing 3-HP.

By using standard cloning techniques and conventional methods known by those skilled in the art, the recombinant microorganism may be obtained by inserting a gene coding for the enzymes which are used in each reduction step into a vector to transform the wild-type microorganism, and culturing the transformed recombinant microorganism. Therefore, a method of converting into general purposed-chemical materials such as 3-HP, a related enzyme, and a recombinant microorganism are provided.

In an embodiment, a method of producing 3-HP using a recombinant microorganism is provided.

3-HP is a weak three carbon non-chiral organic acid having a pKa of 4.51 at 25° C., which is an isomer of 2-hydroxypropionic acid (lactic acid). Furthermore, 3-HP is an amorphous and weak viscous yellow liquid, with a specific gravity of 1.25 and a refractive index of 1.45.

3-HP is very soluble in water, and the calcium salt of 3-HP is 100 times more soluble in water than citric acid or malic acid. Therefore, 3-HP is useful for preventing scale, for example, in a boiler or in industrial equipment. In addition, 3-HP is a critical synthetic intermediate in some chemical processes. Particularly, 3-HP is significant for production of some chemicals and polymers, including production of malic acid by oxidation, production of a biodegradable polymer polyester known as poly(3-hydroxypropionic acid) by esterification with alcohol, and production of 1,3-propanediol (1,3-PDO) by reduction, etc.

3-HP is a critical synthesis intermediate used in various chemical processes, and is used as a source to generate 1,3-propanediol ($C_3H_8O_2$—MW 76.09), acrylic acid ($C_3H_4O_2$—MW 72.06), methyl acrylate ($C_4H_6O_2$—MW 86.09), acrylamide ($C_3H_5NO$—MW 71.08), ethyl 3-hydroxypropionic acid ($C_5H_{10}O_3$—MW 118.13), malonic acid ($C_3H_4O_4$—MW 104.06), propiolactone ($C_3H_4O_2$—MW 72.06), or acrylonitrile ($C_3H_4N$—MW 53.06).

Biosynthetic Pathway of 3-HP

A biosynthetic pathway of 3-HP that is metabolically-engineered using a pathway of producing an intrinsic energy of an organism is provided.

A more host-friendly biofuel system using an intrinsic metabolite of an organism is provided by the biosynthetic pathway for producing a biofuel.

The term "biosynthetic pathway," also referred to as "metabolic pathway," is a set of anabolic or catabolic biochemical reactions for transmuting one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

To describe the 3-HP biosynthetic pathway according to an exemplary embodiment, a pathway using glucose is shown as in FIG. 1.

The 3-HP biosynthetic pathway uses a key metabolic pathway generating energy, i.e., glycolysis for degrading glucose into pyruvate, and conversion of the pyruvate generated by glycolysis into malonyl-CoA via acetyl-CoA (TCA cycle), which are generally known in the art. The method also uses reduction of the malonyl-CoA yielded by these two pathways into malonic semialdehyde, thereby yielding 3-HP. That is, the "malonic semialdehyde reduction pathway" is used.

Therefore, the method of producing 3-HP disclosed herein includes the following steps: reducing acetyl CoA into malonyl CoA, reducing malonyl CoA into malonic semialdehyde, and reducing malonic semialdehyde into 3-HP.

In the step of producing a key metabolite, malonyl-CoA, in the 3-HP biosynthetic pathway, that is, each conversion pathway of the pyruvate→acetyl-CoA→malonyl-CoA pathway, the production efficiency of 3-HP may be decreased due to the presence of the "metabolite leak."

Figure 2:
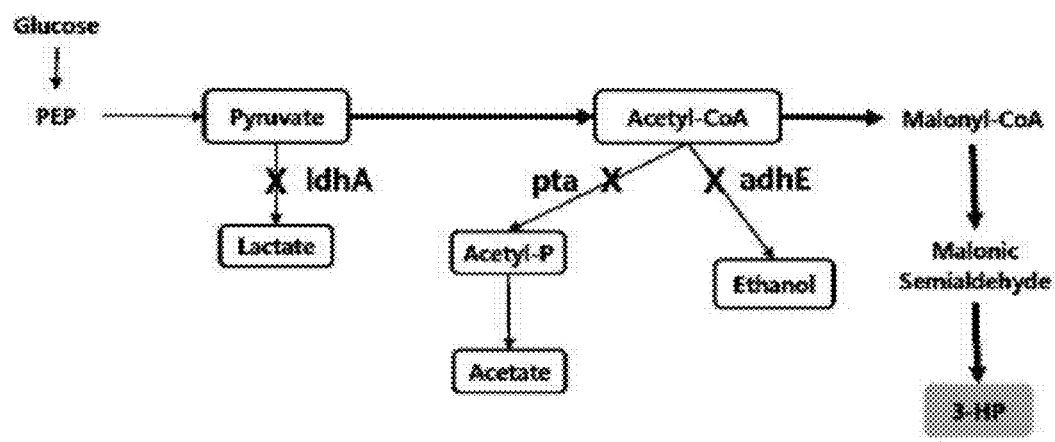
FIG. 2 is a diagram illustrating an effect of gene manipulation by deleting or knocking out ldhA, pda, or adhE to prevent intermediate leak in a metabolic pathway producing 3-HP.
Figure 3:
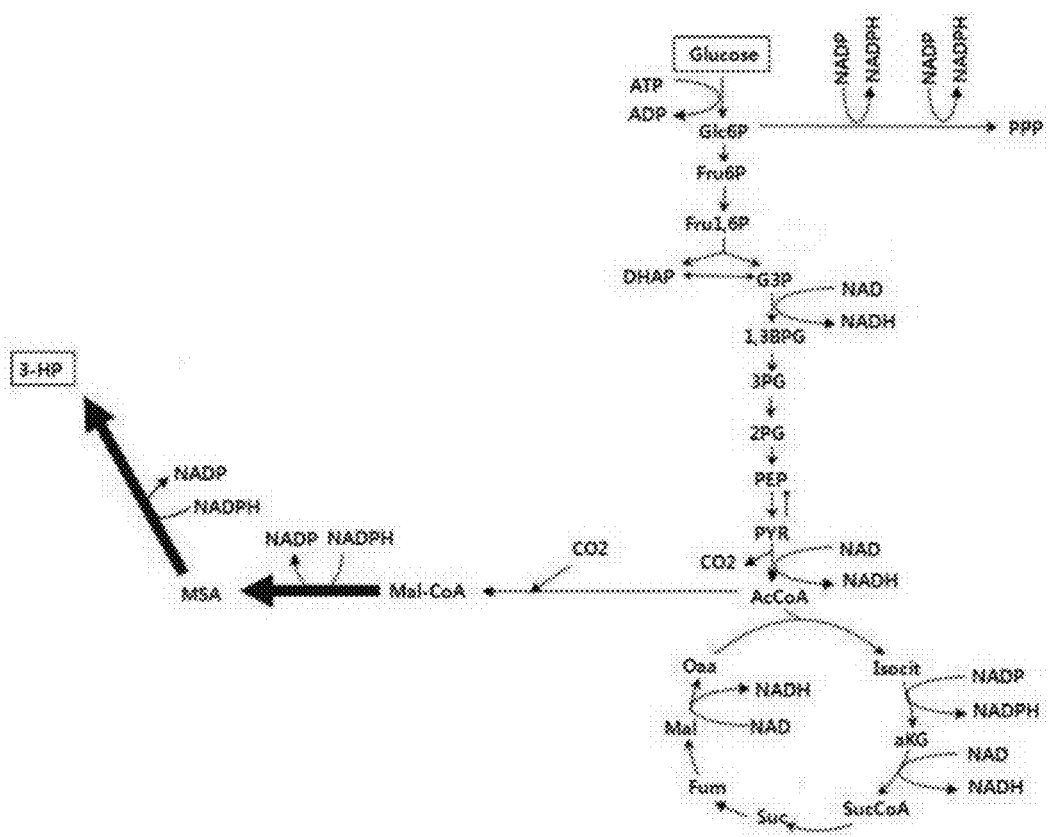
FIG. 3 is a diagram of a basic metabolic pathway producing 3-HP.
Figure 4:
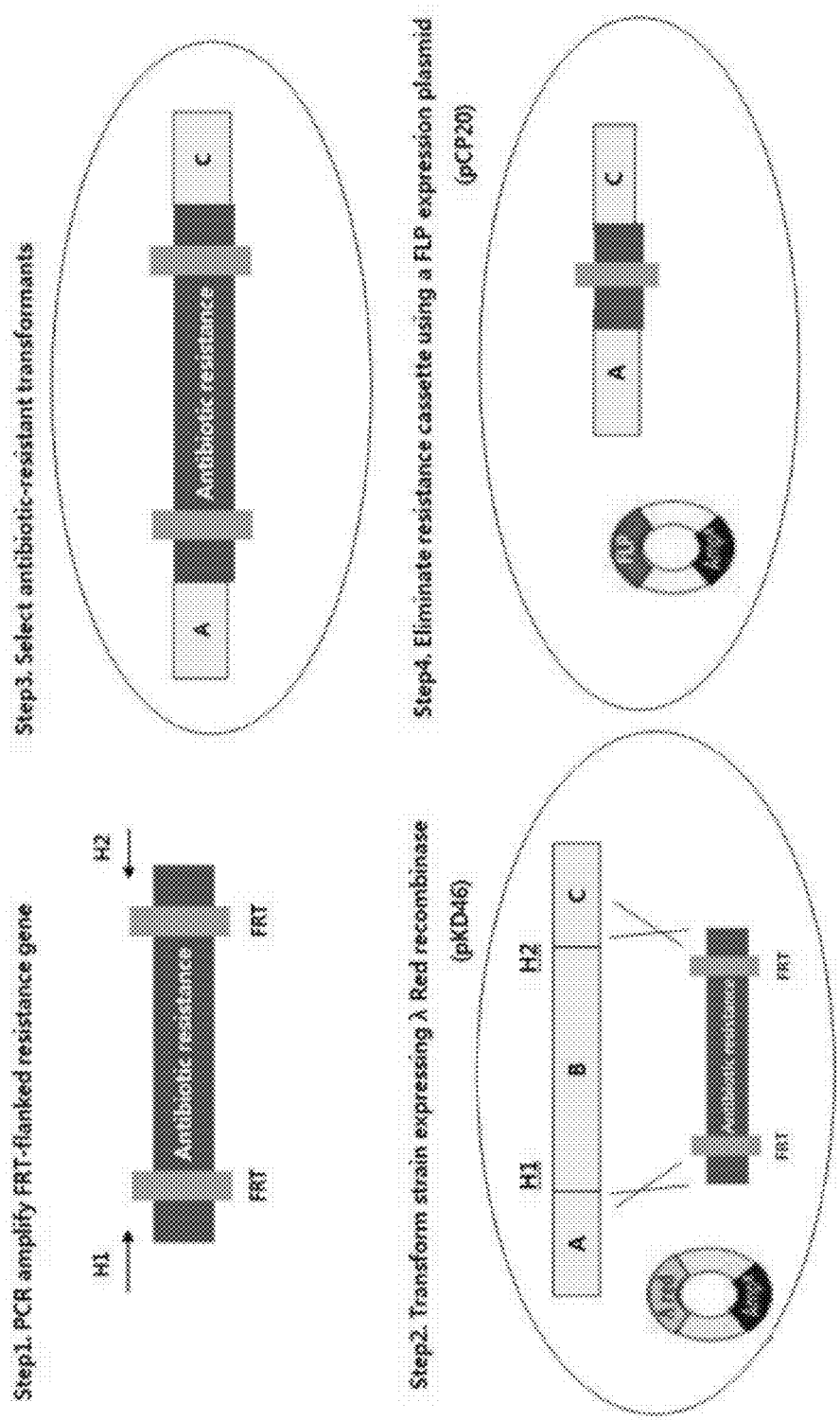
FIG. 4 is a diagram illustrating a process of preparing a recombinant microorganism.

Referring to FIG. 2, first, in the step of converting pyruvate into acetyl-CoA, a lactate may be produced because of the activity of a lactate dehydrogenase. In this case, since the intermediate metabolite of the biosynthetic pathway, or an acetyl-CoA pool, is decreased, it becomes a cause of degrading productivity of 3-HP generated through a subsequent pathway.

In the step of converting acetyl-CoA into malonyl-CoA, acetyl-CoA is converted into acetyl-P and acetate using a phosphotransacetylase ("PTA") and an acetate kinase ("ACK") or converted into ethanol using an acetaldehyde dehydrogenase ("AcDH") and an alcohol dehydrogenase ("ADH"). In this case, a pool of an intermediate metabolite, malonyl-CoA, of the biosynthetic pathway may also be decreased. Therefore, it becomes a cause of degrading productivity of 3-HP generated through a subsequent pathway.

In order to prevent release of such an intermediate metabolite from the 3-HP biosynthetic pathway, transfer of most products to a subsequent pathway has a critical effect on the yield of a final product. Therefore, the metabolite leak may be prevented by inhibiting the activities of the enzymes functioning in respective pathways.

That is, as a pool of acetyl-CoA is increased by preventing the conversion of pyruvate into lactate due to the inhibition of an activity of a lactate dehydrogenase, and a pool of malonyl-CoA is increased by preventing phosphorylation of acetyl-CoA or the conversion into ethanol due to the inhibition of activities of a phosphotransacetylase and an alcohol dehydrogenase, thus ultimately improving a production efficiency of 3-HP.

To this end, metabolism may be manipulated to inhibit expression of the enzymes or prevent activities thereof.

Meanwhile, the 3-HP biosynthetic pathway disclosed herein uses the "malonic semialdehyde reduction pathway," thus using activities of an enzyme reducing malonyl-CoA into malonic semialdehyde and an enzyme reducing malonic semialdehyde into 3-HP. To this end, these activities may be obtained from a recombinant microorganism which is metabolically modified to express or overexpress these activities.

The activity of reducing the malonyl CoA into malonic semialdehyde may be a malonyl-CoA reductase ("mcr") activity, and the activity of reducing the malonic semialdehyde into 3-HP may be a malonate semialdehyde reductase ("msr") activity.

Meanwhile, in the 3-HP biosynthetic pathway disclosed herein, metabolic modification may be performed to express or overexpress an enzyme having an NADPH regeneration activity to resolve redox imbalance.

The activity of regenerating NADPH to increase levels of the NADPH and NADH may be a pyridine nucleotide transhydrogenase activity and/or a glyceraldehyde 3-HP dehydrogenase activity.

In the 3-HP biosynthetic pathway, various enzymes are used to produce various metabolites described above.

A suitable polynucleotide(s) encoding a desired enzyme may be derived from a certain biological source providing the same, and its homologue may be confirmed with reference to various databases.

The native DNA sequence encoding an enzyme described above are referenced herein merely to illustrate an exemplary embodiment, and the embodiment includes DNA molecules of any sequence that encode the amino acid sequence of a polypeptide used in the method. In a similar fashion, a polypeptide may typically tolerate at least one (e.g., two, three, four, five, six, seven, eight, nine, ten, eleven, twelve, thirteen, fourteen, fifteen, sixteen, seventeen, eighteen, nineteen, twenty, or more) amino acid substitution, deletion, and/or insertion in its amino acid sequence without loss or significant loss of a desired activity. Modified polypeptides or variant polypeptides having the enzymatic anabolic or catabolic activity of the wild-type polypeptide are contemplated by the embodiment. Furthermore, the amino acid sequences encoded by the DNA sequences shown herein merely illustrate an exemplary embodiment.

Sequences of the genes and polypeptides/enzymes mentioned above may be easily determined by reference to an available database on the Internet, for example the *E. coli* protein database (EcoPropB), KAIST, 373-1 Guseong-dong, Yuseong-gu Daejeon 305-701, Republic of Korea. In addition, these amino acid and nucleic acid sequences may be easily compared in identity using an algorithm (e.g., BLAST, etc.) generally used in the art.

Recombinant Microorganism

A metabolically engineered microorganism (recombinant microorganism) including a biochemical pathway producing 3-HP from a suitable substrate is provided.

In an embodiment, the metabolically-engineered microorganism includes at least one recombinant polynucleotide inside or outside the genome of the organism. Such a microorganism has a reduction in expression of a gene, a disruption of a gene, or a knockout of a gene, and/or the introduction of a heterologous polynucleotide.

A microbial host for producing 3-HP may be selected from bacteria, cyanobacteria, filamentous fungi, and yeast.

Basically, a microbial host selected to produce 3-HP has resistance to 3-HP, and is capable of converting a carbohydrate into 3-HP. Conditions for selecting a suitable microbial host include: inherent resistance to 3-HP, high glucose utilization, availability of a genetic tool for gene manipulation, and ability to produce stable chromosome alteration. Particularly, in an exemplary embodiment, to prevent the conversion of pyruvate into lactate, the conversion into acetate through phosphorylation of acetyl-CoA, and the conversion of acetyl-CoA into ethanol (i.e., to prevent the metabolite leak in the biosynthetic pathway) a gene encoding at least one enzyme selected from the group consisting of lactate dehydrogenase, phosphotransacetylase, and alcohol dehydrogenase is deleted or knocked out in the microorganism.

Here, a gene encoding the lactate dehydrogenase may be ldhA or a homolog or variant thereof, and a gene encoding the phosphotransacetylase may be pta or a homolog or variant thereof. In addition, the alcohol dehydrogenase may be, for example, ethanol dehydrogenase, and a gene encoding the ethanol dehydrogenase may be adhE or a homolog or variant thereof.

Thus, in a recombinant microorganism according to an exemplary embodiment, at least one of the ldhA, pta, and adhE genes may be deleted or knocked out. In an exemplary embodiment, all of the ldhA, pta and adhE genes are deleted or knocked out.

Accordingly, as the metabolite leak in the 3-HP biosynthetic pathway is blocked, the pool of malonyl-CoA may be increased, and eventually the 3-HP production efficiency using the malonyl semialdehyde reduction pathway may be considerably improved.

A suitable microbial host for producing 3-HP may include at least one genus selected from *Zymomonas, Escherichia, Pseudomonas, Alcaligenes, Salmonella, Shigella, Burkholderia, Oligotropha, Klebsiella, Pichia, Candida, Hansenula, Saccharomyces*, and *Kluyveromyces*, but is not limited thereto.

Among these, at least one genus selected from *Escherichia, Saccharomyces*, and *Kluyveromyces* may be used. For example, *Escherichia coli, Kluyveromyces marxianus, Kluyveromyces fragilis, Kluyveromyces lactis*, or *Sccharomyces cerevisiae* may be used.

In an exemplary embodiment, *E. coli* is used.

Meanwhile, since the 3-HP production using the recombinant microorganism uses the malonic semialdehyde reduction pathway, the recombinant microorganism includes a gene encoding an enzyme that reduces malonyl-CoA into malonic semialdehyde and a gene encoding an enzyme that reduces malonic semialdehyde into 3-HP, in addition to the deletion and knockout of the ldhA, pta, and/or adhE genes.

The enzyme for reducing malonyl-CoA into malonic semialdehyde is a malonyl-CoA reductase ("mcr"), and a gene encoding the enzyme may be a gene derived from *M. sedula*. In addition, the enzyme for reducing malonic semialdehyde into 3-HP is a malonate semialdehyde reductase ("msr"), and a gene encoding the enzyme may also be a gene derived from *M. sedula*.

In addition, the recombinant microorganism may further include a gene encoding an NADPH regeneration enzyme to increase a pool of NADPH and/or NADH to solve redox imbalance.

As the NADPH regeneration enzyme, a pyridine nucleotide transhydrogenase and/or a glyceraldehyde-3-phosphate dehydrogenase may be used. For example, the genes encoding these enzymes, pyridine nucleotide transhydrogenase AB (pntAB) and/or glyceraldehyde-3-phosphate dehydrogenase N (gapN) genes, may be further included. The pntAB gene may be derived from *E. coli*, and gapN gene may be derived from *S. mutants*, but they are not limited thereto.

Deposited recombinant microorganisms corresponding to Deposit Nos. KCTC11947BP, KCTC11948BP, KCTC11949BP, and KCTC11950BP of the Korean Collection for Type Cultures (Korea Research Institute of Bioscience and Biotechnology (KRIBB) 111 Gwahangno, Yuseong-gu, Daejeon 305-806, Republic of Korea; deposited Jun. 10, 2011) can be used in the inventive methods. The deposited microorganisms will be kept in accordance with the terms of the Budapest Treaty, and all restrictions imposed by the depositor on the availability to the public of the deposited material will be irrevocably removed upon the granting of the patent. The deposited microorganisms are merely exemplary, those of ordinary skill in the art may modify a different kind or genotype of an additional parent organism to prepare the microorganism of the disclosure producing 3-HP.

Deposited recombinant microorganisms corresponding to Deposit Nos. KCTC11947BP, KCTC11948BP, KCTC11949BP, and KCTC11950BP of the Korean Collection for Type Cultures (Korea Research Institute of Bioscience and Biotechnology (KRIBB) 111 Gwahangno, Yuseong-gu, Daejeon 305-806, Republic of Korea; deposited Jun. 10, 2011) can be used in the inventive methods. The deposited microorganisms are merely exemplary, those of ordinary skill in the art may modify a different kind or genotype of an additional parent organism to prepare the microorganism of the disclosure producing 3-HP.

Method of Producing 3-HP

According to another aspect, a method of producing 3-HP by culturing the recombinant microorganism is provided.

In detail, the method of producing 3-HP includes incubating the recombinant microorganism in a medium containing a carbon source, and obtaining 3-HP from the incubated microorganism. Here, the incubation of the recombinant microorganism and obtaining 3-HP may be performed using an incubating method generally known in the conventional fermentation industry and a method of isolating and purifying 3-HP.

According to an exemplary embodiment, the method uses a microorganism that performs a process of a metabolic pathway including converting pyruvate into acetyl-CoA, reducing acetyl-CoA into malonyl-CoA, reducing malonyl-CoA into malonic semialdehyde, and reducing malonic semialdehyde into 3-HP. In the step of converting pyruvate into acetyl CoA, activity of at least one enzyme selected from the group consisting of lactate dehydrogenase, phosphotransacetylase, and alcohol dehydrogenase is inhibited.

As described above, the inhibition of the enzyme activity may be performed by deletion or knockout of at least one of ldhA, pta, and adhE, which increases a malonyl-CoA pool in the microorganism (e.g., microbial cell).

The method is performed by incubating a recombinant microorganism in a medium containing a carbon substrate. That is, the method of producing 3-HP uses a carbon source as a substrate.

For example, a carbon source selected from the group consisting of a monosaccharide, an oligosaccharide, a polysaccharide, a C1 substrate, and a mixture thereof may be used. The carbon source may be, but is not limited to, alginate, agar, carrageenan, fucoidan, pectin, gluconate, mannuronate, mannitol, lyxose, cellulose, hemicellulose, glycerol, xylitol, glucose, sucrose, mannose, galactose, xylose, xylan, mannan, arabinan, arabinose, glucuronate, galacturonate (including di- and tri-galacturonates), and rhamnose.

Any one of the carbon substrates and mixtures thereof above is considered suitable for use in the inventive methods under a condition in which an enzyme is reacted. The carbon substrate used to realize the exemplary embodiment may be glucose, sucrose, cellulose or glycerol. In one example, glucose is used.

In addition to the suitable carbon source, the fermentation medium may include a suitable mineral, salt, co-factor, buffer, 3-HP, and/or other components known in the art that are suitable for stimulating an enzyme pathway to produce 1,3-PDO and growing a culture.

Typically, cells are grown at a temperature in the range of about 25° C. to about 40° C. (e.g., 26° C., 28° C., 30° C., 32° C., 34° C., 36° C., or 38° C.) in an appropriate medium. Furthermore, suitable pH for fermentation is between about pH 5.0 to about pH 9.0 (e.g., pH 6.0, pH 7.0, or pH 8.0).

The growth medium can be a commercially prepared medium such as Luria Bertani ("LB") broth, Sabouraud Dextrose ("SD") broth, or Yeast Medium ("YM") broth. Other defined or synthetic growth medium may also be used, and the appropriate medium for the growth of the specific microorganism will be known by one skilled in the art of microbiology or fermentation science. Fermentation may be performed under an aerobic or anaerobic condition.

Likewise, a gene recombinant microorganism according to an exemplary embodiment may prevent conversion into a material other than a desired metabolite, thereby considerably improving producibility of 3-HP.

EXAMPLES

Hereinafter, the invention will be described in further detail with respect to exemplary embodiments. However, it should be understood that the invention is not limited to these Examples and may be embodied in various modifications and changes.

Particularly, in the following Examples, a specific expression vector and *E. coli* host cells are exemplified to express a gene according to the exemplary embodiment, but it is clearly understood by those skilled in the art that various kinds of expression vectors and host cells are also used.

General Methods

Procedures for cloning a standard recombinant DNA and molecules used in the Examples are known in the art. Techniques suitable for use in the following examples may be found in Sambrook et al. [Sambrook, J., Fritsch, E. F. and Maniatis, T., Molecular Cloning: A Laboratory Manual; Cold Spring Harbor Laboratory Press, Cold Spring Harbor, 1989] (hereinafter, referred to as Maniatis), Silhavy et al., Experiments with Gene Fusions, Cold Spring Harbor Laboratory, Cold Spring Harbor, N.Y. 1984, and Ausubel et al., Current Protocols in Molecular Biology, pub. by Greene Publishing Assoc. and Wiley-Interscience, 1987.

Materials and methods suitable for maintenance and growth of a bacterial culture are known in the art. Suitable techniques to be used in the following Examples can be seen in the following: Manual of Methods for General Bacteriology, Phillipp et al., eds., American Society for Microbiology, Washington, D.C., 1994 and Thomas D. Brock, Brock, Biotechnology: A Textbook of Industrial Microbiology, Second Edition, Sinauer Associates, Inc., Sunderland, Mass. (1989).

Gene Cloning (1) Gene Cloning of Malonyl-CoA Reductase ("mcr") and Malonate Semialdehyde Reductase ("msr") from *M. sedula* mcr and msr ("mm") genes use a codon-optimized sequence (Bioneer, Korea) to be expressed in *E. coli*.

(2) Gene Cloning of pntAB from *E. coli* and gapN from *S. mutants* pntAB sequence is obtained by using *E. coli* genome PCR (primer: 5-AATT CCA TGG GA CGA ATT GGC ATA CCA AGA GAA C (SEQ ID NO: 1), 5-AATT GGA TTC TTA CAG AGC TTT CAG GAT TGC ATC (SEQ ID NO: 2)). gapN gene uses a codon optimized sequence to express in *E. coli* (Bioneer, Korea).

Construction of Recombinant Vector

Each plasmid is constructed by the following method.

A. pJYmm01

As an expression vector, pCDFDuet-1 (EMD chemicals) is used, and mcr and msr ("mm") genes uses a codon-optimized sequence (Bioneer, Korea) to be expressed in *E. coli*. The pCDFDuet-1 is digested with restriction enzymes NcoI and HindIII, and ligated into an mm sequence which is digested with the same restriction enzymes, to construct pJYmm01.

B. pJYacc01 acetyl-CoA carboxylase A (accA) sequence from *E. coli* genome is amplified by means of PCR, digested with restriction enzymes NdeI and MfeI, and then ligated into an expression vector, pRSFDuet-1 (EMD chemicals), which is digested with the same restriction enzymes to construct pJYaccA.

Meanwhile, accD sequence from *E. coli* genome is amplified by means of PCR, digested with restriction enzymes NdeI and MfeI, and then ligated into pJYaccA, which is digested with the same restriction enzymes to construct pJYaccAD.

Also, accBC sequence from *E. coli* genome is amplified by means of PCR, digested with restriction enzymes NaeI and XhoI, and then ligated into pJYaccAD, which is digested with the same restriction enzymes to construct pJYacc01.

C. pJYpnt01 pntAB sequence from *E. coli* genome is amplified by means of PCR, digested with restriction enzymes NcoI and BamHI, and then ligated into an expression vector, pRSFDuet-1 (EMD chemicals), which is digested with the same restriction enzymes to construct pJYpnt01.

D. pJYpa01

As an expression vector, pRSFDuet-1 (EMD Chemicals) is used, and the pJYacc01 prepared in B is digested with restriction enzymes NotI and XhoI to obtain an acc sequence. The acc sequence is ligated into pJYpnt01, which is partially digested with the same restriction enzymes to construct pJYpa01.

E. pJYgapN01

As an expression vector, pRSFDuet-1 (EMD Chemicals) is used, and gapN uses a codon-optimized sequence (Bioneer, Korea) to be expressed in *E. coli*. The pRSFDuet-1 is digested with restriction enzymes NcoI and EcoRI, and then ligated into a gapN sequence, which is partially digested with the same restriction enzymes to pJYgapN01.

As an expression vector, pRSFDuet-1 (EMD Chemicals) is used, and the pJYacc01 prepared in B is digested with restriction enzymes NotI and XhoI to obtain an acc sequence. The acc sequence is ligated with pJYpnt01, which is partially digested with the same restriction enzymes to construct pJYgapN01.

F. pJYgNa01

As an expression vector, pRSFDuet-1 (EMD Chemicals) is used, and the pJYacc01 prepared in B is digested with restriction enzymes NotI and XhoI to obtain an acc sequence. The acc sequence is ligated with pJYgapN0, which is partially digested with the same restriction enzymes to construct pJYgNa01.

Example 1

The following example illustrates the preparation of recombinant *E. coli* for producing 3-HP.

The vectors constructed as described above are transformated into *E. coli* by electroporation.

In addition, deletion or disruption of a desired gene is performed by the following method. Here, the literature "One-step inactivation of chromosomal genes in *E. coli* K12 using PCR products (Barry L. Wanner et al., PNAS 2000 (97))" is provided as a reference.

aldH Gene Disruption (i) Amplification of FRT-Flanked Resistance Gene

First, primers (H1 and H2) are constructed using starting and ending fragments of a gene to be disrupted as templates. A kanamycin resistance gene is amplified by PCR using the primers.

(ii) Transformed Strain Expressing λ Red Recombinase (pKD46)

Figure 5:
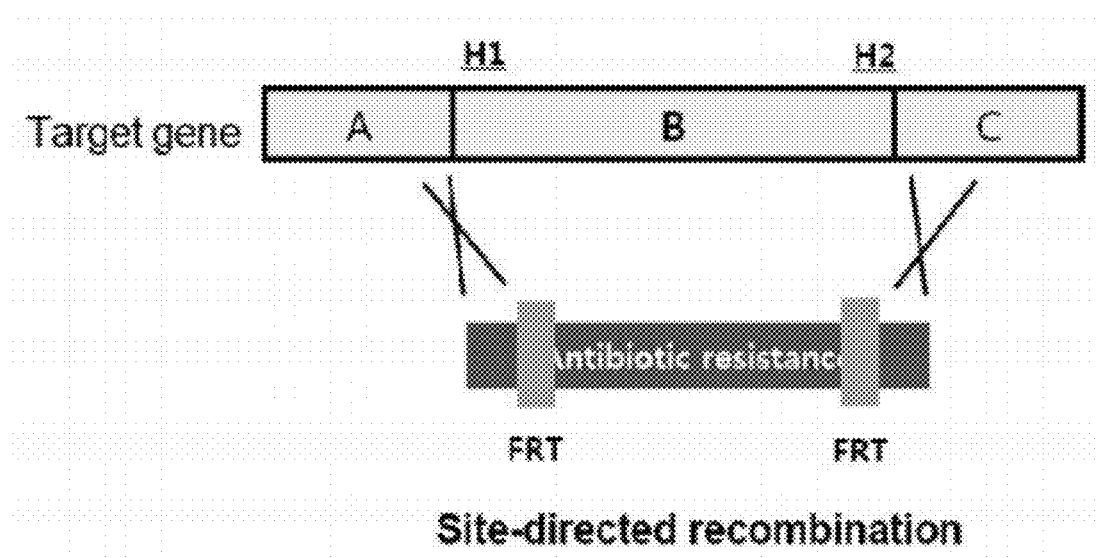
FIG. 5 is an illustration of site-directed recombination by which a target gene is disrupted by replacement of (B) by an FRT-flanked resistance gene. H1 and H2 of FIG. 5 are primers.

The FRT-flanked resistance gene prepared in (i) replaces/disrupts a target gene (B of FIG. 5) due to homologous recombination occurring due to an action of γ Red recombinase in a cell in which pKD46 is transformed.

(1) pKD46 Transformation

A host strain, *E. coli* BL21(DE3), is inoculated into 3 mL LB media (yeast extract 5 g/L, Tryptone 10 g/L, NaCl 10 g/L), and incubated at 37° C. for 12-17 hours in an incubator (200 rpm). After 1 mL of culture solution is transferred to 100 mL LB media, the strain is incubated at 37° C. in an incubator (200 rpm) until the culture approaches to an optical density 600 of 0.4 to 0.5 (exponential phase). In addition, the culture solution is centrifuged at 5000 rpm for 5 minutes, and then a supernatant is discarded to yield only cells. The cells are washed with sterilized DDW, resuspended in 10% glycerol (v/v, pre-chilled), and then centrifuged again three times. Afterward, the cells are resuspended in 1 mL of 10% glycerol.

100 μm of cells are mixed with 2 μm pKD46 (approximately 100 ng), put into a poration cuvette for electroporation, resuspended in 1 mL LB media, and then incubated at 37° C. for 1 hour in an incubator (200 rpm).

Subsequently, to select only pKD46-transformed cells, the incubated cells are spread on an LB+agar+ampicillin (100 μg/L) solid medium and cultured at 37° C. in an incubator under static conditions. After 12 to 16 hours of the culturing, a generated colony is picked and inoculated in 3 mL LB media. The resulting culture is subjected to plasmid mini-preparation to confirm whether pKD46 transformation is properly performed.

(2) Homologous Recombination

An *E. coli* BL21(DE3) pKD46 strain is inoculated in 3 mL LB media and incubated at 37° C. for 12 to 17 hours in an incubator (200 rpm). Then, the procedures described in "1) pKD46 transformation" are performed until the step of resuspending the incubated cells in 1 mL of 10% glycerol.

Subsequently, 100 μl of cells are mixed with approximately 300 ng of PCR fragments of the previously amplified FRT-flanked resistance gene, put into a poration cuvette for electroporation, resuspended in 1 mL LB media, and incubated at 37° C. for 1 hour in an incubator (200 rpm).

To select only cells in which the FRT-flanked resistance genes are recombined, the incubated cells are spread on a LB+agar+kanamycin (50 μg/L) solid medium and cultured at 37° C. in an incubator under static conditions.

(3) Selection of Antibiotic-Resistant Transformants

After a colony formed after 12-16 hours of the culturing is picked and inoculated in 3 mL LB media, 1 mL of cells is centrifuged and resuspended in 200 μl of 10% glycerol. Then, negative PCR is performed. That is, a primer is constructed using a gene sequence missed by disruption as a template, and a strain which does not show a band after PCR, that is, a strain in which a target gene is disrupted, is selected using the primer (when a target gene is disrupted, a corresponding band is not shown, and when a strain is a wild type in which a target gene is not disrupted, an aldH gene PCR band is shown).

To cure a heat-sensitive plasmid pKD46 (remove again in a cell), a selected strain is inoculated in 3 mL LB, and incubated at 42° C. for 24 to 48 hours in an incubator (200 rpm). Subsequently, the culture is streaked simultaneously on LB+agar+kanamycin (50 μg/L) and LB+agar+ampicillin (100 μg/L) solid media to select colonies from which ampicillin resistance is lost.

(4) Removal of Resistance Cassette Using FLP Expression Plasmid (pCP20)

A pCP20-transformed strain is selected by performing the same process of "1) pKD46 transformation" as described in "2) homologous recombination", inoculated in 3 mL LB media, and incubated at 37° C. for 24 hours in an incubator (200 rpm). In this procedure, FLP in pCP20 is expressed, and thus an FRT site is removed. Therefore, a kanamycin resistance gene of an H1-FRT-kanamycin resistance gene-FRT-H2 site is removed, and the resulting product is converted into H1-FRT-H2 from which kanamycin resistance is lost.

Meanwhile, the H1-FRT-H2 is simultaneously streaked on both LB+agar+kanamycin (50 μg/L) and LB+agar solid media to select a colony from which the Kanamycin resistance is lost, and to cure a heat-sensitive plasmid pCP20 (removed again in the cell), and the strain selected as described in "3) Selection of Antibiotic-Resistant Transformants" is inoculated in 3 mL LB and incubated at 42° C. for 24-48 hours in an incubator (200 rpm). The culture is simultaneously streaked on LB+agar and LB+agar+ampicillin (100 μg/L) solid media to select a colony from which ampicillin resistance is lost.

Example 2

The following example illustrates the production of 3-HP using transformed *E. coli*.

Cells of each strain are inoculated in 5 mL LB, and incubated for approximately 18 hours, and the next day, the sufficiently grown cells are inoculated again in 50 mL LB to the same cell concentration. Afterward, the cells are grown until the cell concentration approaches an optical density 600 of 0.6 (37° C., 200 rpm), and 0.1 mM of an inducer (IPTG) is added to express a corresponding gene.

After 44 hours, the culture is sampled and centrifuged for approximately 5 minutes to separate only a supernatant. The supernatant is subjected to HPLC to measure a concentration of 3-HP.

The result is shown in the table below.

| Strain | Strain Description | 3-HP (g/L) |
|---|---|---|
| BL21(DE3)/pJYmm01, pJYacc01 | *Metallosphaera sedula* mcr-msr (gene expression) accABCD (simultaneous gene expression) | 0.01 |
| HPB01f/pJYmm01, pJYacc01 | ΔadhE *Metallosphaera sedula* mcr-msr (gene expression) accABCD (gene expression) | 0.11 |
| HPB02f/pJYmm01, pJYacc01 | ΔldhA *Metallosphaera sedula* mcr-msr (gene expression) accABCD (gene expression) | 0.27 |
| HPB11f/pJYmm01, pJYacc01 | ΔadhE ΔldhA Δpta *Metallosphaera sedula* mcr-msr (gene expression) accABCD (gene expression) | 0.05 |

As seen from the table, to use the "malonic semialdehyde reduction pathway," when the strains are transformed only by a gene encoding acetyl-CoA carboxylase ("acc") showing an activity in the acetyl CoA→malonyl-CoA pathway, a gene encoding malonyl-CoA reductase ("mcr") showing an activity in the malonyl-CoA→malonic semialdehyde pathway, and a gene encoding malonate semialdehyde reductase ("msr") showing an activity in the malonic semialdehyde→3-HP pathway, only 0.01 (g/L) 3-HP is produced. However, when the adhE, the ldhA, or all of the ldhA, pta, and adhE are deleted, 0.11, 0.27 or 0.05 (g/L) 3-HP is produced, respectively. It is confirmed that the production efficiency is increased approximately 5 to 27 times, compared with the conventional art. Particularly, when a recombinant microorganism from which the ldhA is deleted is used, the productivity of 3-HP is noticeably improved.

The terminology used herein is for the purpose of describing particular embodiments only and is not intended to be limiting of the invention. The terms "a" and "an" do not denote a limitation of quantity, but rather denote the presence of at least one of the referenced item.

All methods described herein can be performed in a suitable order unless otherwise indicated herein or otherwise clearly contradicted by context. No language in the specification should be construed as indicating any non-claimed element as essential to the practice of the invention as used herein.

While example embodiments have been disclosed herein, it should be understood that other variations may be possible. Such variations are not to be regarded as a departure from the spirit and scope of example embodiments of the invention, and all such modifications as would be obvious to one skilled in the art are intended to be included within the scope of the following claims.

What is claimed is:

1. A recombinant microorganism for producing 3-hydroxypropionic acid (3-HP), wherein the recombinant microorganism comprises a metabolic pathway in which metabolites are sequentially produced in a sequence of pyruvate, acetyl-CoA, malonyl-CoA and malonic semialdehyde, and comprises a gene encoding an enzyme that reduces malonyl-CoA into malonic semialdehyde and a gene encoding an enzyme that reduces malonic semialdehyde into 3-HP; and wherein the recombinant microorganism has undergone deletion or knockout of a gene encoding at least one selected from the group consisting of lactate dehydrogenase, phosphotransacetylase, and alcohol dehydrogenase.

2. The recombinant microorganism for producing 3-HP of claim 1, wherein the recombinant microorganism belongs to a genus selected from *Escherichia*, *Saccharomyces*, and *Kluyveromyces*.

3. The recombinant microorganism for producing 3-HP of claim 1, wherein the recombinant microorganism is *Escherichia coli*.

4. The recombinant microorganism for producing 3-HP of claim 1, wherein the gene encoding the lactate dehydrogenase is a ldhA or a homolog or variant thereof.

5. The recombinant microorganism for producing 3-HP of claim 1, wherein the gene encoding the phosphotransacetylase is a pta or a homolog or variant thereof.

6. The recombinant microorganism for producing 3-HP of claim 1, wherein the alcohol dehydrogenase is an ethanol dehydrogenase.

7. The recombinant microorganism for producing 3-HP of claim 6, wherein the gene encoding the ethanol dehydrogenase is adhE or a homolog or variant thereof.

8. The recombinant microorganism for producing 3-HP of claim 1, wherein the recombinant microorganism has undergone deletion or knockout of the genes encoding lactate dehydrogenase, phosphotransacetylase, and alcohol dehydrogenase.

9. The recombinant microorganism for producing 3-HP of claim 1, wherein the recombinant microorganism reduces or inhibits conversion of pyruvate into lactate, conversion of acetyl-CoA into acetyl phosphate (acetyl P), or conversion of acetyl-CoA into ethanol.

10. The recombinant microorganism for producing 3-HP of claim 1, wherein the recombinant microorganism is a microorganism deposited in the Korean Collection for Type Cultures as Deposit No. KCTC11947BP, KCTC11948BP, KCTC11949BP, or KCTC11950BP.

11. The recombinant microorganism for producing 3-HP of claim 1, wherein the gene encoding an enzyme that reduces malonyl-CoA into malonic semialdehyde is a gene encoding a malonyl-CoA reductase (mcr), and the gene encoding an enzyme that reduces malonic semialdehyde into 3-HP is a gene encoding a malonate semialdehyde reductase (msr).

12. The recombinant microorganism for producing 3-HP of claim 1, wherein the recombinant microorganism further comprise a gene encoding an NADPH regeneration enzyme.

13. The recombinant microorganism for producing 3-HP of claim 12, wherein the gene encoding the NADPH regeneration enzyme is a gene encoding a transhydrogenase or a gene encoding a glyceraldehyde-3-phosphate dehydrogenase.

14. The recombinant microorganism for producing 3-HP of claim 13, wherein the gene encoding the transhydrogenase is pyridine nucleotide transhydrogenase (pntAB) or soluble pyridine nucleotide transhydrogenase (udhA), and the gene encoding the glyceraldehyde-3-phosphate dehydrogenase is non-phosphorylating glyceraldehyde-3-phosphate dehydrogenase (gapN).

15. A method of producing 3-HP in a recombinant microorganism according to claim 1, the method comprising:
converting pyruvate into acetyl-CoA;
converting acetyl-CoA into malonyl-CoA;
converting malonyl-CoA into malonic semialdehyde; and
converting malonic semialdehyde into 3-HP,
wherein, during the conversion of pyruvate into acetyl-CoA, an activity of at least one enzyme selected from the group consisting of lactate dehydrogenase, phosphotransacetylase, and alcohol dehydrogenase is inhibited in the microorganism.

16. The method of producing 3-HP of claim 15, wherein the inhibition of the enzyme activity is performed by deletion or knockout of at least one gene selected from the group consisting of adhE, pta, and adhE in the microorganism.

17. The method of producing 3-HP of claim 15, wherein the method increases malonyl-CoA pools in a microbial cell.

18. The method of producing 3-HP of claim 15, wherein the method is performed by incubating the recombinant microorganism in a medium containing a carbon substrate.

19. The method of producing 3-HP of claim 18, wherein the carbon substrate is at least one selected from the group consisting of glucose, sucrose, cellulose, and glycerol.

* * * * *